US008923943B2

(12) United States Patent
Benni

(10) Patent No.: US 8,923,943 B2
(45) Date of Patent: *Dec. 30, 2014

(54) METHOD FOR SPECTROPHOTOMETRIC BLOOD OXYGENATION MONITORING

(71) Applicant: CAS Medical Systems, Inc., Branford, CT (US)

(72) Inventor: Paul B. Benni, Acton, MA (US)

(73) Assignee: CAS Medical Systems, Inc., Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/793,964

(22) Filed: Mar. 11, 2013

(65) Prior Publication Data
US 2014/0094668 A1  Apr. 3, 2014

Related U.S. Application Data

(63) Continuation of application No. 11/914,074, filed as application No. PCT/US2006/018082 on May 10, 2006, now Pat. No. 8,396,526.

(60) Provisional application No. 60/680,192, filed on May 12, 2005.

(51) Int. Cl.
*A61B 5/00* (2006.01)

(52) U.S. Cl.
USPC .......................................... 600/323; 600/331

(58) Field of Classification Search
CPC ........... A61B 5/14551; A61B 5/14552; A61B 5/1495
USPC .......................................... 600/323, 331, 232
See application file for complete search history.

(56) References Cited

U.S. PATENT DOCUMENTS

| 3,638,640 A | 2/1972 | Shaw |
| 4,281,645 A | 8/1981 | Jobsis |
| 4,570,638 A | 2/1986 | Stoddart et al. |
| 4,714,341 A | 12/1987 | Hamaguri et al. |
| 4,725,147 A | 2/1988 | Stoddart |

(Continued)

FOREIGN PATENT DOCUMENTS

| WO | 0184107 | 11/2001 |
| WO | 2004010844 | 2/2004 |

OTHER PUBLICATIONS

Benni et al.: "A Novel Near-Infrared Spectroscopy (NIRS) System for Measuring Regional Oxygen Saturation", Department of Anesthesia, Robert Wood Johnson Medical School, May 22, 1995.

(Continued)

*Primary Examiner* — Max Hindenburg
(74) *Attorney, Agent, or Firm* — O'Shea Getz P.C.

(57) ABSTRACT

According to the present invention, a method and apparatus for non-invasively determining the blood oxygen saturation level within a subject's tissue is provided. The method includes the steps of: a) providing a spectrophotometric sensor operable to transmit light into the subject's tissue, and to sense the light; b) detecting light after passage through the subject's tissue using the sensor, and producing initial signal data from the light sensed; c) calibrating the sensor to that particular subject using the initial signal data, thereby accounting for the specific physical characteristics of the particular subject's tissue being sensed; and d) using the calibrated sensor to determine the blood oxygen parameter value within the subject's tissue.

14 Claims, 3 Drawing Sheets

(56) References Cited

U.S. PATENT DOCUMENTS

| | | |
|---|---|---|
| 4,768,516 A | 9/1988 | Stoddart et al. |
| 4,805,623 A | 2/1989 | Jobsis |
| 4,817,623 A | 4/1989 | Stoddart et al. |
| 4,907,876 A | 3/1990 | Suzuki et al. |
| 5,040,539 A | 8/1991 | Schmitt et al. |
| 5,054,488 A | 10/1991 | Muz |
| 5,139,025 A | 8/1992 | Lewis et al. |
| 5,153,669 A | 10/1992 | DeGroot |
| 5,218,962 A | 6/1993 | Mannheimer et al. |
| 5,251,632 A | 10/1993 | Delpy |
| 5,299,579 A | 4/1994 | Gedeon et al. |
| 5,348,004 A | 9/1994 | Hollub |
| 5,349,961 A | 9/1994 | Stoddart et al. |
| 5,413,100 A | 5/1995 | Barthelemy et al. |
| 5,421,329 A | 6/1995 | Casciani et al. |
| 5,482,034 A | 1/1996 | Lewis et al. |
| 5,517,987 A | 5/1996 | Tsuchiya |
| 5,524,617 A | 6/1996 | Mannheimer |
| 5,529,065 A | 6/1996 | Tsuchiya |
| 5,632,273 A | 5/1997 | Suzuki |
| 5,676,142 A | 10/1997 | Miwa et al. |
| 5,706,821 A | 1/1998 | Matcher et al. |
| 5,770,454 A | 6/1998 | Essenpreis et al. |
| 5,772,589 A | 6/1998 | Bernreuter |
| 5,782,756 A | 7/1998 | Mannheimer |
| 5,803,909 A | 9/1998 | Maki et al. |
| 5,853,370 A | 12/1998 | Chance et al. |
| 5,902,235 A | 5/1999 | Lewis et al. |
| 6,192,260 B1 | 2/2001 | Chance |
| 6,456,862 B2 | 9/2002 | Benni |
| 6,512,936 B1 | 1/2003 | Monfre et al. |
| 6,516,209 B2 | 2/2003 | Cheng et al. |
| 6,615,065 B1 | 9/2003 | Barrett et al. |
| 6,882,874 B2 | 4/2005 | Huiku |
| 7,029,444 B2 | 4/2006 | Shin et al. |
| 7,072,701 B2 | 7/2006 | Chen et al. |
| 8,396,526 B2 * | 3/2013 | Benni .......................... 600/323 |

OTHER PUBLICATIONS

Jacques et al: "The Melanosome: Threshold Temperature for Explosive Vaporization and Internal Absorption Coefficient During Pulsed Laser Irradiation", Photchemistry and Photobiology, vol. 53, No. 6, pp. 769-775, 1991.

\* cited by examiner

METHOD FOR SPECTROPHOTOMETRIC BLOOD OXYGENATION MONITORING

This application is a continuation of U.S. patent application Ser. No. 11/914,074 filed Nov. 9, 2007, now issued as U.S. Pat. No. 8,396,526, which application is a national stage application of PCT Patent Application No. PCT/US06/18082 filed May 10, 2006 which claims priority to U.S. Provisional Patent Application No. 60/680,192 filed May 12, 2005, the disclosures of which are herein incorporated by reference.

This invention was made with Government support under Contract No. 2R44NS045488-02 awarded by the Department of Health & Human Services. The Government has certain rights in the invention.

BACKGROUND OF THE INVENTION

1. Technical Field

This invention relates to methods for non-invasively determining biological tissue oxygenation in general, and to non-invasive methods utilizing near-infrared spectroscopy (NIRS) techniques for determining the same in particular.

2. Background Information

U.S. Pat. No. 6,456,862 and U.S. Pat. No. 7,072,701, both assigned to the assignee of the present application and both hereby incorporated by reference, disclose methods for spectrophotometric blood oxygenation monitoring. Oxygen saturation within blood is defined as:

$$O_2 \text{ saturation } \% = \frac{HbO_2}{(HbO_2 + Hb)} * 100\% \quad \text{(Eqn. 1)}$$

These methods, and others known within the prior art, utilize variants of the Beer-Lambert law to account for optical attenuation in tissue at a particular wavelength. Relative concentrations of oxyhemoglobin ($HbO_2$) and deoxyhemoglobin (Hb), and therefore oxygenation levels, within a tissue sample are determinable using changes in optical attenuation:

$$\Delta A_\lambda = -\log\left(\frac{I_{t2}}{I_{t1}}\right)_\lambda = \alpha_\lambda * \Delta C * d * B_\lambda \quad \text{(Eqn. 2)}$$

wherein "$A_\lambda$" represents the optical attenuation in tissue at a particular wavelength $\lambda$ (units: optical density or OD); "I" represents the incident light intensity (units: W/cm$^2$); "$\alpha_\lambda$" represents the wavelength dependent absorption coefficient of the chromophore (units: OD* cm$^{-1}$*µM$^{-1}$); "C" represents the concentration of chromophore (units: µM); "d" represents the light source to detector (optode) separation distance (units: cm); and "$B_\lambda$" represents the wavelength dependent light scattering differential pathlength factor (unitless)

To non-invasively determine oxygen saturation within tissue accurately, it is necessary to account for the optical properties (e.g., absorption coefficients or optical densities) of the tissue being interrogated. In some instances, the absorption coefficients or optical densities for the tissue components that create background light absorption and scattering can be assumed to be relatively constant over a selected wavelength range. The graph shown in FIG. 1, which includes tissue data plotted relative to a Y-axis of values representative of absorption coefficient values and an X-axis of wavelength values, illustrates such an instance. The aforesaid constant value assumption is reasonable in a test population where all of the subjects have approximately the same tissue optical properties; e.g., skin pigmentation, muscle and bone density, etc. A tissue interrogation method that relies upon such an assumption may be described as being wavelength independent within the selected wavelength range and subject independent. Our findings indicate that the same assumption is not reasonable, however, in a population of subjects having a wide spectrum of tissue optical properties (e.g., a range of significantly different skin pigmentations from very light to very dark) unless consideration for the wide spectrum of tissue optical properties is provided otherwise.

What is needed, therefore, is a method for non-invasively determining the level of oxygen saturation within biological tissue that accounts for optical influences from the specific tissue through which the light signal passes.

DISCLOSURE OF THE INVENTION

According to one aspect of the present invention, a method and apparatus for non-invasively determining the blood oxygen saturation level within a subject's tissue is provided. In one embodiment, the method includes the steps of: 1) providing a near infrared spectrophotometric sensor operable to transmit light along a plurality of wavelengths into the subject's tissue; 2) sensing the light transmitted into the subject's tissue using the sensor, and producing signal data representative of the light sensed from the subject's tissue; 3) processing the signal data, including accounting for physical characteristics of the subject; and 4) determining the blood oxygen saturation level within the subject's tissue using a difference in attenuation between the wavelengths.

The apparatus includes at least one sensor having at least one light source and at least one light detector, which sensor is operably connected to a processor. The light source is operable to transmit light along a plurality of wavelengths into the subject's tissue, and to produce signal data representative of the light sensed from the subject's tissue. The algorithm selectively produces calibration constants for use with the sensor that account for the specific physical characteristics of the particular subject being sensed. The calibration constants are produced using the signal data.

According to another aspect of the present invention, a method for calibrating a NIRS sensor is provided that includes the steps of: 1) transmitting light into a subject's tissue using the sensor; 2) sensing the light using the sensor along a plurality of wavelengths after the light travels through the subject's tissue, and producing signal data from the sensed light; and 3) calibrating the sensor using the signal data.

The present method and apparatus provides advantageous accuracy. All prior art non-invasive devices and methods for determining blood oxygen saturation level within a subject's tissue, of which we are aware, do not consider the specific physical characteristics of the particular subject being sensed. The sensor is calibrated by use of assumed constants and/or relative to a source (e.g., a phantom sample, empirical data, etc.) other than the subject being sensed; i.e., calibrated in a "subject independent" manner. The present device and method, in contrast, considers the specific physical characteristics (e.g., tissue pigment, muscle and bone density and mass, etc.) of the particular subject by initially sensing the subject's tissue, creating signal data based on the sensing, and accounting for the specific physical characteristics of the subject using the signal data. The sensor, now calibrated in a "subject dependent" manner, can be used determine the tissue blood oxygen saturation level of the subject tissue. As a result, the sensor is able to provide a more accurate assessment of the subject's blood oxygen saturation level within the tissue being sensed.

Another advantage of the present method and apparatus is that accurate blood oxygen saturation level information can be provided for a population of subjects having a wide range of physical characteristics. Physical characteristics (e.g., tissue pigmentation, thickness and density, etc.) naturally vary between subjects, and those characteristics create differences in light attenuation, background scattering and absorption. The present method and apparatus considers the physical characteristics of the specific subject being tested, and calibrates the sensor with signal data generated from sensing the tissue of the specific subject. Consequently, the present method and device accounts for the differences in light attenuation specific to that subject and enables the tissue blood oxygenation saturation level of subjects having a wide range of physical characteristics to be accurately sensed.

These and other objects, features, and advantages of the present invention method and apparatus will become apparent in light of the detailed description of the invention provided below and the accompanying drawings. The methodology and apparatus described below constitute a preferred embodiment of the underlying invention and do not, therefore, constitute all aspects of the invention that will or may become apparent by one of skill in the art after consideration of the invention disclosed overall herein.

DETAILED DESCRIPTION THE INVENTION

The present method of and apparatus for non-invasively determining the blood oxygen saturation level within a subject's tissue is provided that utilizes a near infrared spectrophotometric (NIRS) sensor that includes a transducer capable of transmitting a light signal into the tissue of a subject and sensing the light signal once it has passed through the tissue via transmittance or reflectance. The present method and apparatus can be used with a variety of NIRS sensors, and is not therefore limited to any particular NIRS sensor.

Figure 2:
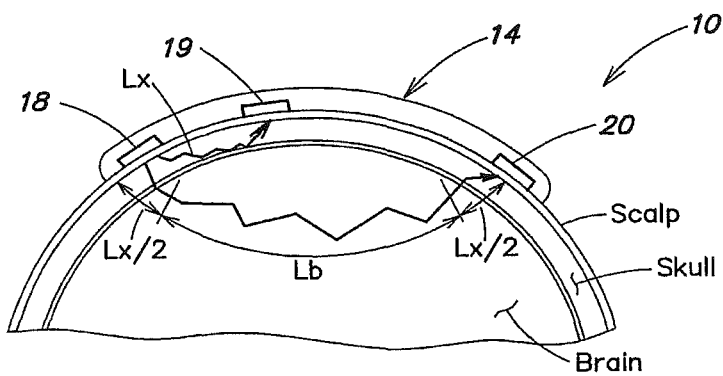
FIG. 2 is a diagrammatic representation of a NIRS sensor.
Figure 3:
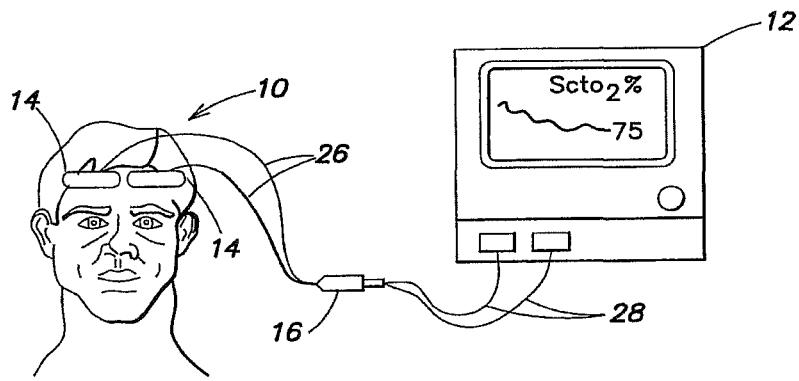
FIG. 3 is a diagrammatic representation of a NIRS sensor placed on a subject's head.
Figure 4:
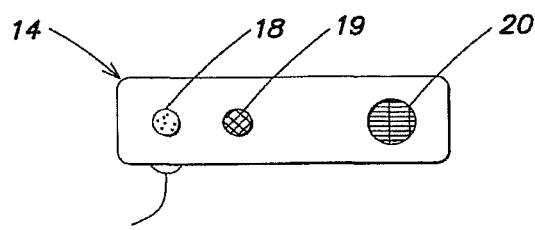
FIG. 4 is a diagrammatic view of a NIRS sensor.

Referring to FIGS. 2-4, an example of an acceptable NIRS sensor includes a transducer portion 10 and processor portion 12. The transducer portion 10 includes an assembly housing 14 and a connector housing 16. The assembly housing 14, which is a flexible structure that can be attached directly to a subject's body, includes one or more light sources 18 and light detectors 19, 20. A disposable adhesive envelope or pad is preferably used for mounting the assembly housing 14 easily and securely to the subject's skin. Light signals of known but different wavelengths from the light sources emit through a prism assembly. The light sources 18 are preferably laser diodes that emit light at a narrow spectral bandwidth at predetermined wavelengths. The laser diodes may be mounted remote from the assembly housing 14; e.g., in the connector housing 16 or within the processor portion 12. In these embodiments, a fiber optic light guide is optically interfaced with the laser diodes and the prism assembly that is disposed within the assembly housing 14. In other embodiments, the light sources 18 are mounted within the assembly housing 14. A first connector cable 26 connects the assembly housing 14 to the connector housing 16 and a second connector cable 28 connects the connector housing 16 to the processor portion 12. The light detectors 19, 20 each include one or more photodiodes. The photodiodes are also operably connected to the processor portion 12 via the first and second connector cables 26, 28. Other examples of acceptable NIRS sensors are described in U.S. Patent Application No. 60/751, 009 filed on Dec. 16, 2005, and U.S. Patent Application No. 60/729,339 filed on Oct. 21, 2005, both of which applications are commonly assigned to the assignee of the present application and both of which are hereby incorporated by reference in their entirety.

The processor portion 12 includes a processor for processing light intensity signals associated with the light sources 18 and the light detectors 19, 20 as described herein. A person of skill in the art will recognize that the processor may assume various forms (e.g., digital signal processor, analog device, etc.) capable of performing the functions described herein. The processor utilizes an algorithm that characterizes a change in attenuation as a function of the difference in attenuation between different wavelengths. The algorithm accounts for the effects of pathlength and parameter "E", which represents energy losses ("G") due to light scattering within tissue, other background absorption losses ("F") from biological compounds, and other unknown losses ("N") including measuring apparatus variability (E=G+F+N). As will be discussed below, the parameter "E" reflects energy losses not specific to the subject being tested with a calibrated sensor (i.e., "subject-independent").

The absorption $A_{b\lambda}$ detected from the deep light detector 20 includes attenuation and energy losses from both the deep and shallow tissue, while the absorption $A_{x\lambda}$ detected from the shallow light detector 19 includes attenuation and energy losses from shallow tissue. Absorptions $A_{b\lambda}$ and $A_{x\lambda}$ can be expressed in the form of Equation 3 and Equation 4:

$$A_{b\lambda} = -\log\left(\frac{I_b}{I_o}\right) = \alpha_\lambda * C_b * L_b + \alpha_\lambda * C_x * L_x + E_\lambda \quad \text{(Eqn. 3)}$$

$$A_{x\lambda} = -\log\left(\frac{I_b}{I_o}\right)_\lambda = \alpha_\lambda * C_x * L_x + E_{x\lambda} \quad \text{(Eqn. 4)}$$

In some applications (e.g., infants), a single light detector may be used, in which case Equation 5 is used:

$$A_{b\lambda} = -\log(I_b/I_o)_\lambda = \alpha_\lambda * C_b * L_b + E_\lambda \quad \text{(Eqn 5)}$$

If both the deep and shallow detectors are used, then substituting Equation 4 into Equation 3 yields $A'_\lambda$, which represents attenuation and energy loss from deep tissue only:

$$A'_\lambda = A_{b\lambda} - A_{x\lambda} = \alpha_\lambda * C_b * L_b + (E_\lambda - E_{x\lambda}) \quad \text{(Eqn. 6)}$$

From Equation 5 or Equation 6, L is the effective pathlength of the photon traveling through the deep tissue and $A'_1$ and $A'_2$ represent light attenuation at two different wavelengths to determine differential wavelength light attenuation $\Delta A'_{12}$:

$$A'_1 - A'_2 = \Delta A'_{12} \quad \text{(Eqn. 7)}$$

Substituting Equation 5 or 6 into Equation 7 for $A'_1$ and $A'_2$, $\Delta A'_{12}$ can be expressed as:

$$\Delta A'_{12} = \alpha_{\lambda 12} * C_b * L_b + \Delta E'_{12} \quad \text{(Eqn. 8)}$$

and Equation 8 can be rewritten in expanded form:

$$\Delta A'_{12} = \langle (\alpha_{r1} - \alpha_{r2})[Hb]_b + (\alpha_{o1} - \alpha_{o2})[HbO_2]_b \rangle L_b + (E'_1 - E'_2) = (\Delta\alpha_{r12}*[Hb]_b*L_b) + (\Delta\alpha_{o12}*[HbO_2]_b*L_b) + \Delta E'_{12} \quad \text{(Eqn. 9)}$$

where:

$(\Delta\alpha_{r12}*[Hb]_b*L_b)$ represents the attenuation attributable to Hb; and $(\Delta\alpha_{o12}*[HbO_2]_b*L_b)$ represents the attenuation attributable to $HbO_2$; and $\Delta E'_{12}$ represents energy losses due to light scattering within tissue, other background absorption losses from biological compounds, and other unknown losses including measuring apparatus variability.

The multivariate form of Equation 9 is used to determine $[HbO_2]_b$ and $[Hb]_b$ with three different wavelengths:

$$\begin{bmatrix} \Delta A'_{12} & \Delta E'_{12} \\ \Delta A'_{13} & \Delta E'_{13} \end{bmatrix} (L_b)^{-1} = \begin{bmatrix} \Delta\alpha_{r12} & \Delta\alpha_{o12} \\ \Delta\alpha_{r13} & \Delta\alpha_{o13} \end{bmatrix} \begin{bmatrix} [Hb]_b \\ [HbO_2]_b \end{bmatrix} \quad \text{(Eqn. 10)}$$

Rearranging and solving for $[HbO_2]_b$ and $[Hb]_b$, simplifying the $\Delta\alpha$ matrix into $[\Delta\alpha']$:

$$\begin{bmatrix} \Delta A'_{12} \\ \Delta A'_{13} \end{bmatrix} [\Delta\alpha']^{-1} (L_b)^{-1} - \begin{bmatrix} \Delta E'_{12} \\ \Delta E'_{13} \end{bmatrix} [\Delta\alpha']^{-1} (L_b)^{-1} = \begin{bmatrix} [Hb]_b \\ [HbO_2]_b \end{bmatrix} \quad \text{(Eqn. 11)}$$

Then combined matrices $[\Delta A'] [\Delta\alpha']^{-1} = [A_c]$ and $[\Delta E] [\Delta\alpha]^{-1} = [\Psi_c]$:

$$\begin{bmatrix} A_{Hb} \\ A_{HbO_2} \end{bmatrix} (L_b)^{-1} - \begin{bmatrix} \Psi_{Hb} \\ \Psi_{HbO_2} \end{bmatrix} (L_b)^{-1} = \begin{bmatrix} [Hb]_b \\ [HbO_2]_b \end{bmatrix} \quad \text{(Eqn. 12)}$$

The parameters $A_{Hb}$ and $A_{HbO2}$ represent the product of the matrices $[\Delta A_\lambda]$ and $[\Delta\alpha']^{-1}$ and the parameters $\Psi_{Hb}$ and $\Psi_{HbO2}$ represent the product of the matrices $[\Delta E'_2]$ and $[\Delta\alpha']^{-1}$. To determine the level of cerebral tissue blood oxygen saturation ($SnO_2$), Equation 12 is rearranged using the form of Equation 1 and is expressed as follows:

$$SnO_2\% = \frac{(A_{HbO_2} - \Psi_{HbO_2})}{(A_{HbO_2} - \Psi_{HbO_2} + A_{Hb} - \Psi_{Hb})} * 100\% \quad \text{(Eqn. 13)}$$

Note that tissue blood oxygen saturation is sometimes symbolized as $StO_2$, $SctO2$, $CrSO_2$, or $rSO_2$. The effective pathlength $L_b$ cancels out in the manipulation from Equation 12 to Equation 13.

The value for $SnO_2$ is initially determined from an empirical reference of weighted combination of venous and arterial oxygen saturation ($SmvO_2$) value, for example using:

$$SmvO_2 = Kv*SvO_2 + Ka*SaO_2 \quad \text{(Eqn. 14)},$$

and the empirically determined values for $SvO_2$ and $SaO_2$, where the term "$SvO_2$" represents venous oxygen saturation, the term "$SaO_2$" represents arterial oxygen saturation, and the terms Kv and Ka are the weighted venous and arterial contributions respectively (Kv+Ka=1). The empirically determined values for $SvO_2$ and $SaO_2$ are based on data developed by discrete sampling or continuous monitoring of the subject's blood performed at or about the same time as the sensing of the tissue with the sensor; e.g., blood samples discretely collected can be analyzed by blood gas analysis and blood samples continuously monitored can be analyzed using a fiber optic catheter inserted within a blood vessel. The temporal and physical proximity of the NIRS sensing and the development of the empirical data helps assure accuracy. The initial values for Kv and Ka within Equation 14 are clinically reasonable values for the circumstances at hand. The values for $A_{HbO2}$ and $A_{Hb}$ are determined mathematically using the values for $I_{b\lambda}$ and $I_{x\lambda}$ for each wavelength sensed with the NIRS sensor (e.g., using Equation 3 & 4 for deep and shallow detectors or Equation 5 for a single detector). The calibration parameters $\Psi_{Hb}$ and $\Psi_{HbO2}$, which account for energy losses due to scattering as well as other background absorption from biological compounds, are then determined using Equation 14 and non-linear regression techniques by correlation to different weighted values of $SvO_2$ and $SaO_2$; i.e., different values of Ka and Kv. Statistically acceptable values of Kv and Ka and $\Psi_{Hb}$ and $\Psi_{HbO2}$ are converged upon using the non-linear regression techniques. Experimental findings show that with proper selection of Ka and Kv, the calibration parameters $\Psi_{Hb}$ and $\Psi_{HbO2}$ are constant within a statistically acceptable margin of error for an individual NIRS sensor used to monitor brain oxygenation on different human subjects.

The above-identified process produces a NIRS sensor calibrated relative to a particular subject using invasive techniques, or a NIRS sensor calibrated relative to an already calibrated sensor (or relative to a phantom sample). When these calibrated sensors are used thereafter on a different subject, they do not account for the specific physical characteristics of the particular subject being tested. The present method and apparatus as described below permits a NIRS sensor to be calibrated in a non-invasive manner that accounts for specific physical characteristics of the particular subject being sensed.

Certain physical characteristics will vary from subject to subject, such as but not limited to, tissue pigmentation and thickness and density of muscle and/or bone. The present method and apparatus accounts for background tissue's wavelength dependent light attenuation differences due to these subject-dependent physical characteristics by sensing the subject's tissue, creating signal data from the sensing, and using the signal data to create one or more "subject-specific" calibration constants that account for the specific characteristics of the subject. For example, during an initial phase of monitoring, light is transmitted into and sensed passing out of the subject's tissue. Signal data representative of the sensed light is analyzed to account for the physical characteristics of the subject, and one or more subject-specific calibration constants indicative of the specific physical characteristics are created. The subject-specific calibration constants are subsequently used to determine properties such as the blood oxygen saturation level, deoxyhemoglobin concentration, oxyhemoglobin concentration, etc.

The subject-specific calibration constants can be determined by using the sensed signal data to create a tissue optical property (TOP) index value. The TOP index value is derived from wavelength dependent light attenuation attributable to physical characteristics such as tissue pigmentation, thickness and density of tissue, etc. These physical characteristics are collectively considered in determining the TOP index value because the characteristics have absorption coefficients that increase with decreasing wavelength from the near-infrared region to the red region (i.e., from about 900 nm to about 400 nm) mainly due to the presence of melanin, the light absorbing pigmentation in skin and tissue. For example, it has been reported by S. L. Jacques et al., that light absorption in skin due to melanin can be described by the relationship: $\mu_a = 1.70 \times 10^{12}$ (wavelength in nm)$^{-3.48}$ [cm$^{-1}$] in the wavelength range from about 400 nm to about 850 nm. If the overall light absorption characteristics of tissue are modeled to follow that of melanin, then the TOP light absorption coefficients ($\alpha_{Top}$) can be determined using the same equation for the particular wavelengths of light used in the interrogation of the tissue (where $A=1.7 \times 10^{12}$ and $T=-3.48$):

$$\alpha_{TOP} = A^*(\text{wavelength})^{-T} \quad \text{(Eqn. 15)}$$

To determine the TOP index value, one or more of the wavelengths in the near-infrared region to the red region (i.e., from about 900 nm to about 600 nm; e.g., 690 nm, 780 nm, 805 nm, 850 nm) are sensed. Red wavelengths are favored because red light is more sensitive to the tissue optical properties than infrared light. Lower wavelengths of light could also be used, but suffer from increased attenuation from the higher tissue and hemoglobin absorption coefficients, resulting in reduced tissue penetration, reduced detected light signal strength, and resultant poor signal to noise ratio.

To calculate the TOP index value (identified in Equation 16 as "TOP"), a four wavelength, three unknown differential attenuation algorithm (following similarly to the derivation shown by Equations 3-10), is used such as that shown in Equation 16:

$$\begin{bmatrix} \Delta A'_{12} \\ \Delta A'_{13} \\ \Delta A'_{14} \end{bmatrix} (L_b)^{-1} = \begin{bmatrix} \Delta\alpha'_{r12} & \Delta\alpha'_{o12} & \Delta\alpha'_{TOP12} \\ \Delta\alpha'_{r13} & \Delta\alpha'_{o13} & \Delta\alpha'_{TOP13} \\ \Delta\alpha'_{r14} & \Delta\alpha'_{o14} & \Delta\alpha'_{TOP14} \end{bmatrix} \begin{bmatrix} Hb \\ HbO_2 \\ TOP \end{bmatrix} \quad \text{(Eqn. 16)}$$

Alternatively, Equation 17 shown below could be used. Equation 17 accounts for energy losses "E" as described above:

$$\begin{bmatrix} \Delta A'_{12} & \Delta E'_{12} \\ \Delta A'_{13} & \Delta E'_{13} \\ \Delta A'_{14} & \Delta E'_{14} \end{bmatrix} (L_b)^{-1} = \quad \text{(Eqn. 17)}$$

$$\begin{bmatrix} \Delta\alpha'_{r12} & \Delta\alpha'_{o12} & \Delta\alpha'_{TOP12} \\ \Delta\alpha'_{r13} & \Delta\alpha'_{o13} & \Delta\alpha'_{TOP13} \\ \Delta\alpha'_{r14} & \Delta\alpha'_{o14} & \Delta\alpha'_{TOP14} \end{bmatrix} \begin{bmatrix} Hb \\ HbO_2 \\ TOP \end{bmatrix}$$

The TOP index value determinable from Equations 16 or 17 accounts for subject tissue optical properties variability and can be converted to a "corrective" factor used to determine accurate tissue blood oxygen saturation $SnO_2$. In some embodiments, the TOP index value can be used with a database to determine subject-specific calibration constants (e.g., $Z_{Hb}$ and $Z_{HbO2}$). The database contains data, at least some of which is empirically collected, pertaining to oxyhemoglobin and deoxyhemoglobin concentrations for a plurality of subjects. The concentration data is organized relative to a range of TOP index values in a manner that enables the determination of the subject-specific calibration constants. The organization of the information within the database can be accomplished in a variety of different ways.

Figure 1:
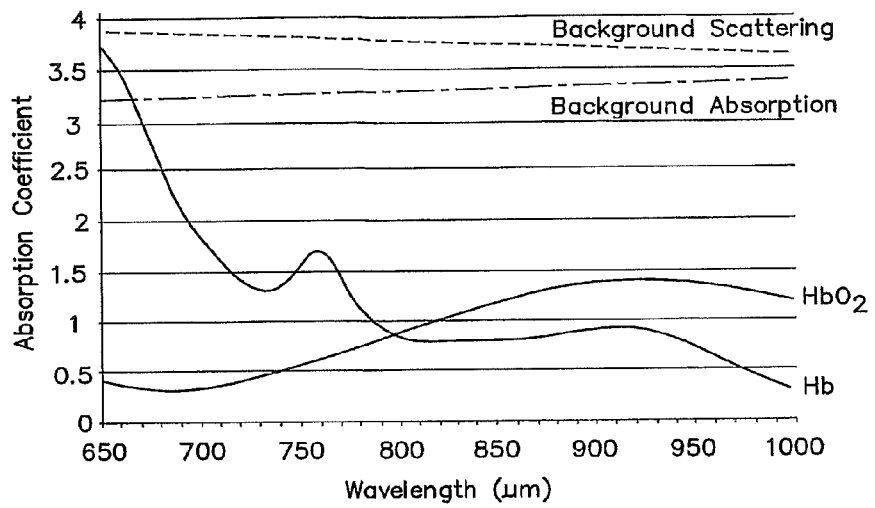
FIG. 1 is a graph diagrammatically illustrating tissue data plotted relative to a Y-axis of values representative of absorption coefficient values, and an X-axis of wavelength values.
Figure 5:
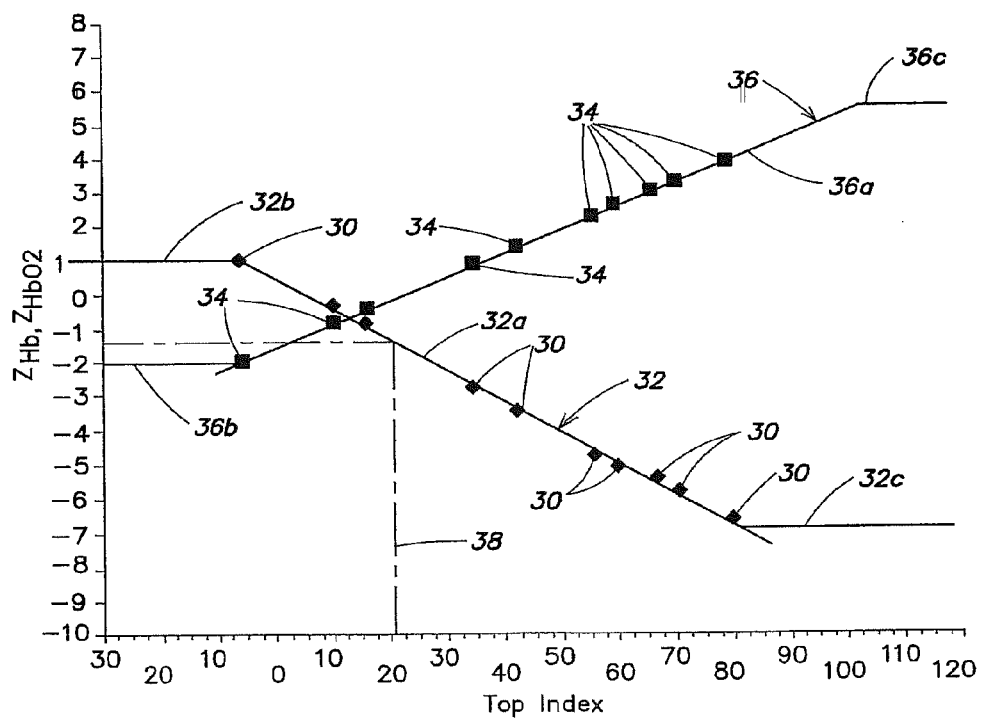
FIG. 5 is a graph having values diagrammatically representative of subject-specific calibration coefficients plotted along a Y-axis, TOP index values plotted along an X-axis, and data representative of deoxyhemoglobin values and oxyhemoglobin values plotted therebetween with best-fit curves applied thereto.

For example, the empirical database may be organized in the form of a graph having subject-specific calibration coefficients plotted along the y-axis versus TOP index values plotted along the x-axis. An example of such a graph is shown in FIG. 5, which contains data 30 representing the differences between calculated deoxyhemoglobin values (Hb) values and empirically derived deoxyhemoglobin values (the differences referred to in FIG. 5 as "Hb-offset2 data"), and a best fit curve 32 applied to a portion of that data 30. The graph also contains data 34 representing the differences between calculated oxyhemoglobin values (HbO2) values and empirically derived oxyhemoglobin values (the differences referred to in FIG. 5 as "Hb02-offset2 data"), and another best-fit curve 36 applied to a portion of that data 34. In the example shown in FIG. 5, a statistically significant number of the data 30, 34 for each curve lies within the sloped portion 32a, 36a (i.e., the portion that does not have a constant calibration constant value). At each end of the sloped portion 32a, 36a, the curves 32, 36 are depicted as having constant calibration values 32b, 32c, 36b, 36c for convenience sake. The values for the subject-specific calibration coefficients $Z_{Hb}$ and $Z_{HbO2}$ are determined by drawing a line (e.g., see phantom line 38) perpendicular to the TOP index value axis at the determined TOP index value. The subject-specific calibration constant ($Z_{Hb}$) for deoxyhemoglobin is equal to the value on the calibration constant axis aligned with the intersection point between the perpendicular line and the "Hb-offset2" curve, and the subject-specific calibration constant ($Z_{HbO2}$) for oxyhemoglobin is equal to the value on the calibration constant axis aligned with the intersection point with the "HbO2-offset2" curve.

Alternatively, the subject-specific calibration constant values may be determined using an empirical database in a form other than a graph. For example, a mathematical solution can be implemented rather than the above-described graph. The mathematical solution may use linear equations representing the "Hb-offset2" and the "HbO2-offset2" curves.

Once the subject-specific calibration constant values are determined, they are utilized with a variation of Equation 13:

$$SnO_2\% = \frac{(A_{HbO_2} - \Psi_{HbO_2} + Z_{HbO_2})}{\left(\begin{array}{c} A_{HbO_2} - \Psi_{HbO_2} + Z_{HbO_2} + \\ A_{Hb} - \Psi_{Hb} + Z_{Hb} \end{array}\right)} * 100\% \quad \text{(Eqn. 18)}$$

to determine the cerebral blood oxygen saturation level.

Figure 6:
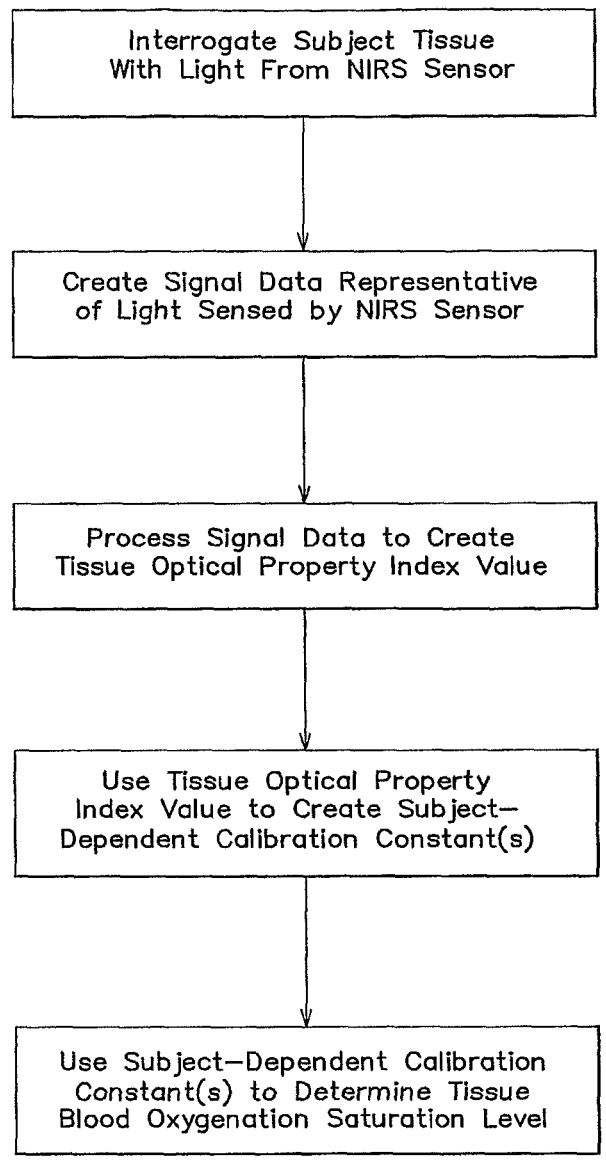
FIG. 6 is a flow chart illustrating steps according to one aspect of the present invention.

The above-described process for determining the subject-specific calibration constants can be performed one or more times in the initial period of sensing the subject to calibrate the sensor to that particular subject, preferably right after the sensor is attached to the subject. The subject-dependent calibration constants can then be used with an algorithm for measurement of a subject's blood oxygen saturation level using the same or different signal data. The algorithm in which the subject-dependent calibration constants are utilized may be the same algorithm as used to determine the constants, or a different algorithm for determining the tissue oxygen saturation level. For example, calibration constants can be used with the three wavelength method disclosed above in Equations 2-14, and in U.S. Pat. No. 6,456,862, which is hereby incorporated by reference. Prior to the cerebral blood oxygen saturation level being calculated, the subject-specific calibration constants $Z_{Hb}$ and $Z_{HbO2}$ can be incorporated as corrective factors into the three wavelength algorithm (e.g., incorporated into Eqn. 13). As a result, a more accurate determination of the subject's tissue oxygen saturation level is possible. FIG. 6 illustrates the above described steps within a flow chart.

In alternative embodiments, the TOP index methodology disclosed above can be used within an algorithm in a subject-independent manner. This approach does not provide all of the advantages of the above described subject-dependent methodology and apparatus, but does provide improved accuracy by specifically accounting for subject skin pigmentation. For example, the TOP absorption coefficients can be determined as described above and utilized within Equation 16 or Equation 17. Regardless of the equation used, the determined values for deoxyhemoglobin (Hb) and oxyhemoglobin (HbO$_2$) can subsequently be used to determine the tissue oxygen saturation level. For example, the Hb and HbO$_2$ values can be utilized within Equations 11 through 13.

Although the present method and apparatus are described above in terms of sensing blood oxygenation within cerebral tissue, the present method and apparatus are not limited to cerebral applications and can be used to determine tissue blood oxygenation saturation within tissue found elsewhere within the subject's body. If the present invention is utilized to determine the tissue blood oxygenation saturation percentage is typically symbolized as StO$_2$ or rSO$_2$.

Since many changes and variations of the disclosed embodiment of the invention may be made without departing from the inventive concept, it is not intended to limit the invention otherwise than as required by the appended claims.

What is claimed is:

1. A method for non-invasively determining a blood oxygen parameter value of a subject's tissue, comprising the steps of:
    providing a spectrophotometric sensor operable to transmit light into the subject's tissue, and to sense the light;
    detecting light after passage through the subject's tissue using the sensor, and producing initial signal data from the light sensed;
    calibrating the sensor to that particular subject using the initial signal data, thereby accounting for the specific physical characteristics of the particular subject's tissue being sensed; and
    subsequent to calibrating the sensor, using the calibrated sensor to determine the blood oxygen parameter value within the subject's tissue.

2. The method of claim 1, wherein the blood oxygen parameter is oxyhemoglobin.

3. The method of claim 1, wherein the blood oxygen parameter is deoxyhemoglobin.

4. The method of claim 3, wherein the calibrating step includes processing the signal data to consider pigmentation of the subject's tissue.

5. The method of claim 4, wherein the processing step includes the use of absorption coefficients for pigmentation in the subject's tissue.

6. The method of claim 1, wherein the step of determining the blood oxygen parameter value within the subject's tissue comprises processing signal data other than the initial signal data.

7. An apparatus for non-invasively determining a blood oxygen saturation level of the microvasculature within a subject's tissue, the apparatus comprising:
    a spectrophotometric sensor operable to transmit light into the subject's tissue, to detect the light after passage through the subject's tissue using the sensor, and to produce initial signal data from the light sensed;
    a processor adapted to calibrate the sensor to that particular subject using the initial signal data, thereby accounting for the specific physical characteristics of the particular subject's tissue being sensed, and adapted to use the calibrated sensor to determine the blood oxygen saturation level within the subject's tissue.

8. The apparatus of claim 7, wherein the physical characteristics of the subject's tissue include pigmentation of skin and tissue disposed below the skin.

9. The apparatus of claim 8, wherein the processor is adapted to create absorption coefficients representative of the pigmentation of the skin and tissue below the skin.

10. The apparatus of claim 9, wherein the processor is adapted to determine one or more calibration constants using the absorption coefficients for pigmentation, which calibration constants are used to determine the blood oxygen saturation level within the subject's tissue.

11. The apparatus of claim 7, wherein the sensor is adapted to produce initial signal data that is attributable to non-pulsatile blood flow within the microcirculation of the subject's tissue.

12. The apparatus of claim 7, wherein the processor is adapted to determine the blood oxygen saturation level within the subject's tissue using signal data other than the initial signal data.

13. The apparatus of claim 7, wherein the processor is adapted to determine the concentration of at least one of oxyhemoglobin and deoxyhemoglobin of the microvasculature within the subject's tissue using the calibrated sensor.

14. The apparatus of claim 7, wherein the spectrophotometric sensor includes at least one light source and at least one light detector, wherein the light source is operable to transmit light along a plurality of wavelengths into the subject's tissue, and the light detector is operable to detect light from the light source after the light has traveled through the subject's tissue.

* * * * *